United States Patent [19]

Thompson, Johnnie W.

[11] 4,451,939
[45] Jun. 5, 1984

[54] KNEE JOINT APPARATUS FOR A LEG PROSTHESIS

[76] Inventor: Thompson, Johnnie W., Rte. 3, Box 263, Pelzer, S.C. 29699

[21] Appl. No.: 226,813

[22] Filed: Jan. 21, 1981

[51] Int. Cl.³ .............................................. A61F 1/04
[52] U.S. Cl. ........................................ 3/23; 308/217; 3/27
[58] Field of Search .................... 3/22, 23, 26, 27, 28; 308/217

[56] References Cited

U.S. PATENT DOCUMENTS

| | | | |
|---|---|---|---|
| 2,863,684 | 12/1958 | Carroll | 3/28 |
| 2,870,453 | 1/1959 | Vasquez | 3/26 |
| 2,943,622 | 7/1960 | Nelson | 3/27 |
| 3,673,613 | 7/1972 | Asbelle et al. | 3/28 |
| 4,003,609 | 1/1977 | Juhas | 308/217 |

FOREIGN PATENT DOCUMENTS

| | | | |
|---|---|---|---|
| 168889 | 9/1957 | Austria | 3/27 |
| 474290 | 9/1952 | Italy | 3/23 |
| 548958 | 10/1956 | Italy | 3/23 |
| 336757 | 10/1930 | United Kingdom | 3/28 |

OTHER PUBLICATIONS

Horn, "Electro-Control: An EMG-Controlled A/K Prosthesis", Med. & Biol. Engng., vol. 10, pp. 61-73, Pergamon Press 1972.

Primary Examiner—Richard J. Apley
Assistant Examiner—David J. Isabella
Attorney, Agent, or Firm—Dority & Flint

[57] ABSTRACT

Rotary joint apparatus for a prosthesis and the like having a first section 10 and a second section 16 joined by the joint is disclosed including a housing member A connected to one of the sections and a housing member B connected to the other of said sections. A shaft C rotatably connects the housing members. A roller bearing clutch assembly D rotatably connects the housing member B to shaft C and includes an outer bearing race 18 connected to housing member B having a plurality of circumferentially spaced tapered camming portions 32 forming generally wedge-shaped camming surfaces. A plurality of roller bearings 34 are positioned in the camming portions bearing against shaft C. The roller bearings have a first position in the camming portion in which the bearings are locked between a surface 32b of the camming portion and shaft C for locking and preventing rotation relative to the shaft in a first direction. The roller bearings have a second position in said camming portion in which said bearings are free between a camming portion surface 32a and the shaft permitting rotation between said shaft and housing member. Operator members E are carried concentric with shaft C and are operatively connected with roller bearings 34 for shifting position of the roller bearings in the camming portions. The clutch operator members have an unlocked position in which the clutch assembly is unlocked and the roller bearings are held in the second position to permit rotation in the first direction. The operator members have a clutch mode position in which the roller bearings are held thereby in their first position and rotation in the first direction is permitted. An actuator member, responsive to pressure on a portion of said foot prosthesis, is connected to the operator members for positioning the operator members in the unlocked and clutch positions.

2 Claims, 9 Drawing Figures

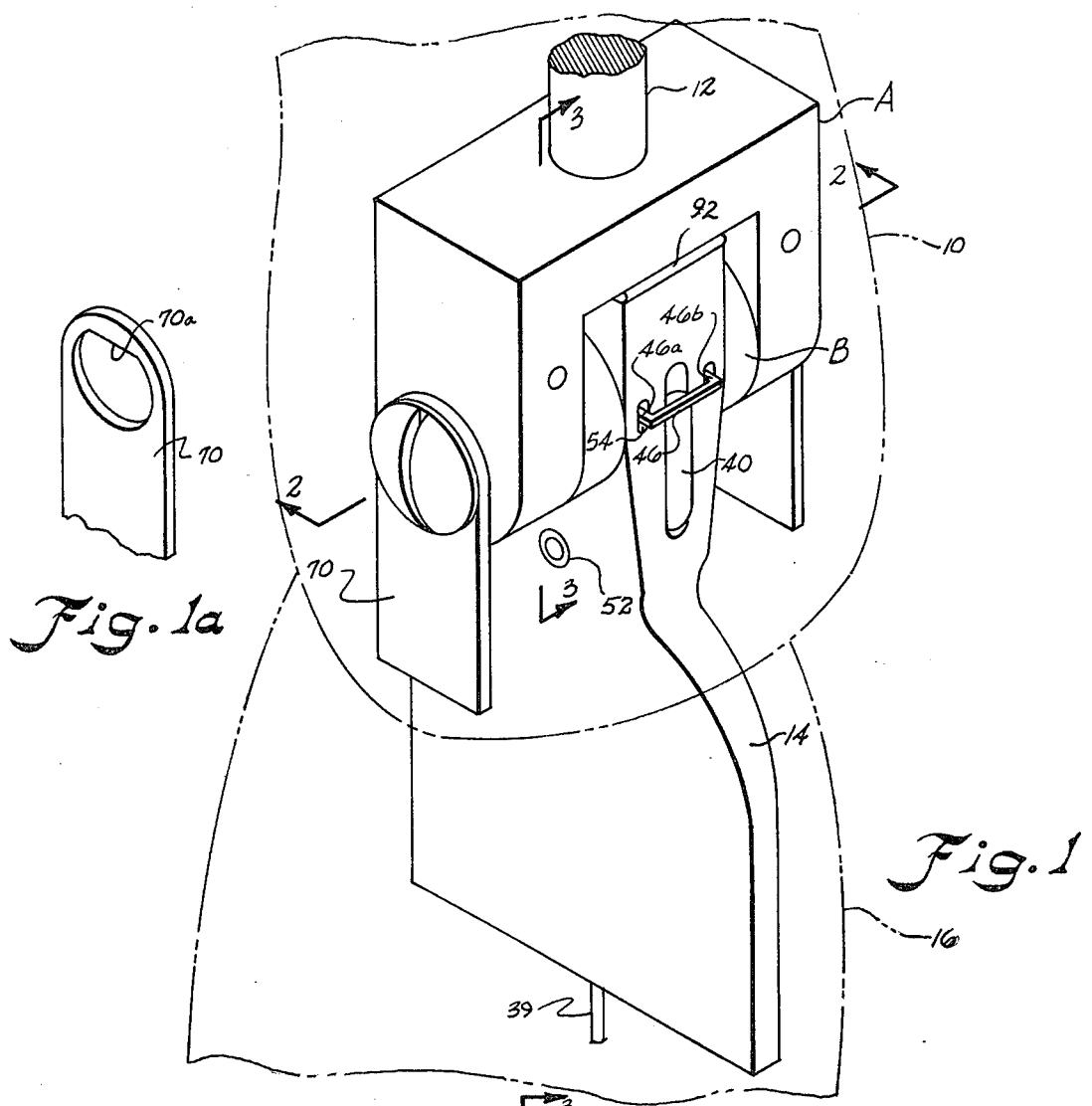
Fig. 1a
Fig. 1
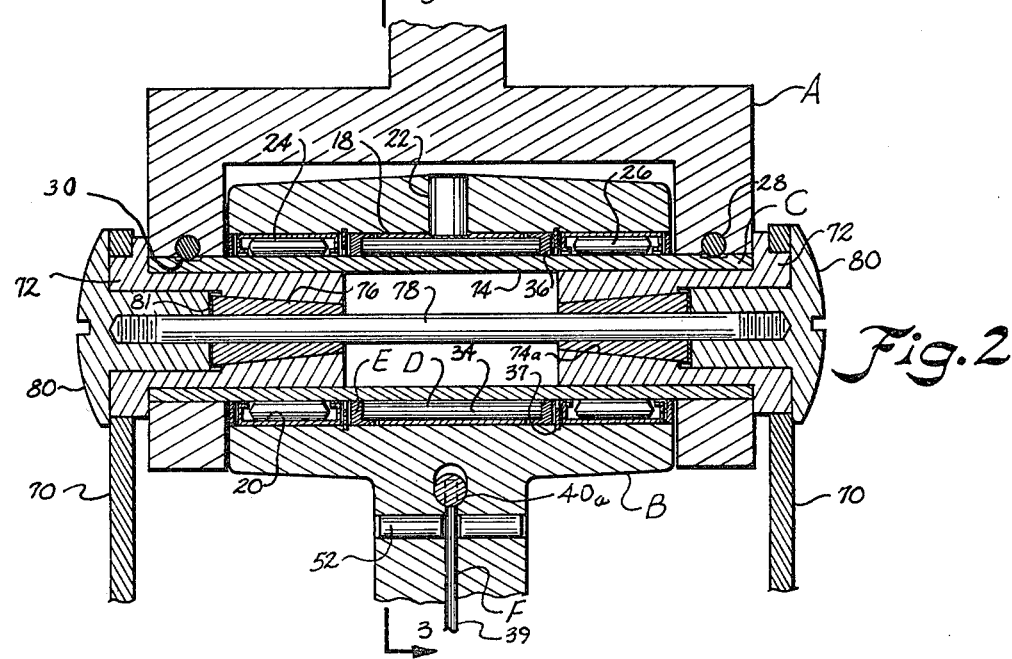
Fig. 2

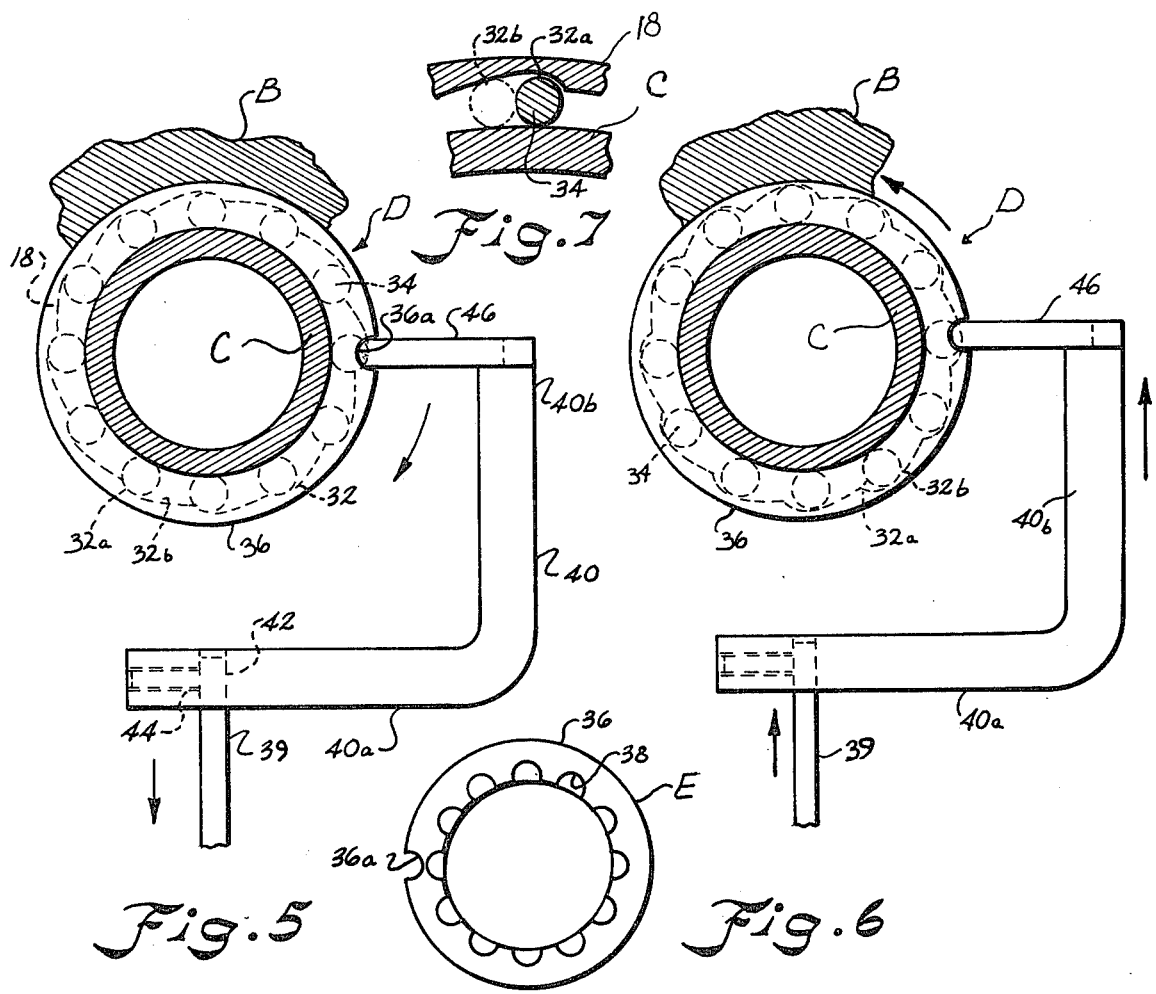
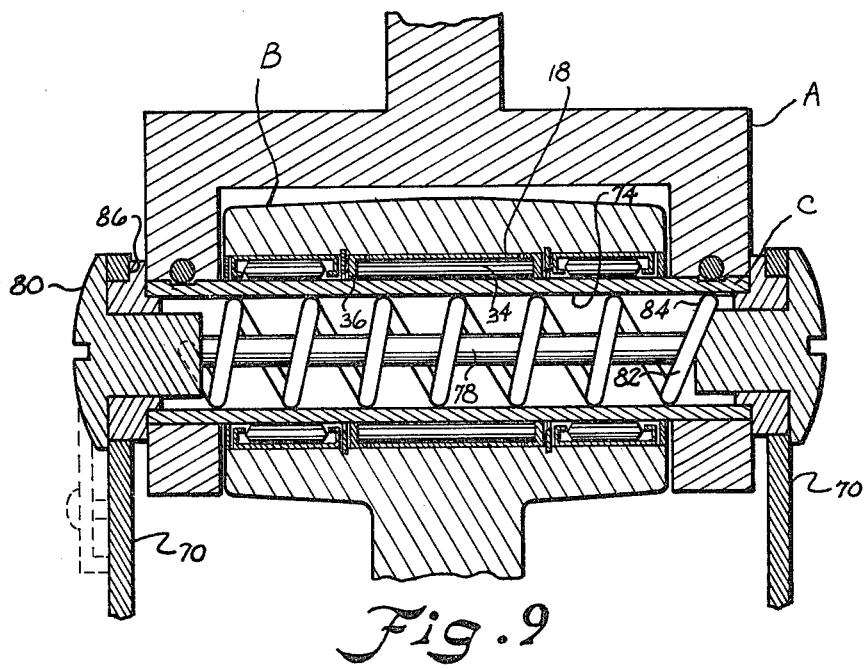

KNEE JOINT APPARATUS FOR A LEG PROSTHESIS

BACKGROUND OF THE INVENTION

This invention relates to a leg prosthesis and, more particularly, to a knee joint for a leg prosthesis which is automatically locked when weight is placed on the leg.

Heretofore, attempts have been made to provide artificial legs having mechanical knee joints which are automatically locked and unlocked while the wearer is walking to simulate a natural knee action and walking gait. However, these devices have resulted in rather complex mechanical mechanisms for the knee joint action and have not altogether provided a simplified reliable actuating mechanism for locking the knee joint in a weight supporting configuration. A typical device utilizing a ratchet and pawl mechanism for the knee joint is shown in U.S. Pat. Nos. 2,943,622 and 2,071,711.

An improved operating mechanism for operating a mechanical knee joint is disclosed in applicant's U.S. Pat. No. 4,090,264 which employs a ratchet-type joint and reliable actuating member which are particularly suitable for a heavy person.

Another development for locking a knee joint in a leg prosthesis has been by means of a mechanical clutch released by an electrical control pulse which is derived from the myoelectric activity of the patient's stump. This features enables the amputee to use the artificial leg as a reaction point for his residual muscles. Such a development is disclosed in an article by G. W. Horn entitled "Electro-Control: EMG-Controlled A/K Prosthesis" appearing in *Medical and Biological Engineering*, Vol. 10, pp. 64–73, Pergamon Press, 1972. However, the user must be trained and skilled in the control of the muscles in his stump to control the knee joint and the knee can only be folded after the mechanism is automatically reset after the leg has been fully extended. Spring force is utilized to position the roller clutch assembly which can vary and thus is lacking in positive, reliable control thereof.

Accordingly, an important object of the present invention is to provide an artificial knee joint for a leg prosthesis which is simplified in construction and reliable in operation.

Yet another important object of the present invention is to provide knee-joint structure for a leg prothesis which has very few moving parts and is lightweight and may be easily incorporated into a lightweight leg prothesis; and which, by virtue of having fewer moving parts, is less susceptible to wear and misadjudgment of the knee joint.

Yet another important object of the present is to provide a knee joint for a leg prothesis employing a mechanical roller clutch assembly which is controlled by positive direct mechanical actuation.

Yet another important object of the present invention is to provide artificial knee joint apparatus having a roller clutch assembly which locks the lower leg from folding when weight is placed on the leg, but otherwise is unlocked to allow the lower leg section to swing in any direction.

Yet another important object of the present invention is to provide artificial knee joint apparatus in employing a roller clutch assembly having a positive locking and unlocking action which allows the lower leg section to be folded anytime there is no weight present upon the foot portion of the prosthesis.

Yet another important object of the present invention is to provide a knee-joint structure for a leg prothesis having an adjustable drag system for controlling the swing speed of the leg.

SUMMARY OF THE INVENTION

It has been found that the above objectives can be achieved according to the present invention by providing a knee joint apparatus which includes a roller clutch assembly having an outer bearing race connected to a lower leg section through which a shaft is received which connects the lower leg section to an upper leg section. A plurality of camming portions are formed in the interior surface of the outer bearing race, and a plurality of roller bearings are positioned within the camming portions in between the outer race and the shaft. The roller bearings have a first clutch position in the camming portion wherein the camming portion urges the roller bearings in locking connection against the shaft which prevents rotation of the lower leg section relative to the shaft in a first direction which corresponds to the folding direction of the lower leg section. The roller bearings have a second position in the camming portion wherein the bearings are not engaged with the shaft and rotation of the lower leg section about the shaft via the bearing race is permitted in any direction. A clutch operator member operatively connected to the roller bearings has a first position positively holding the roller bearings in their first or clutch position and a second position in which the operator member holds the roller bearings in their second position in the camming portions which unlocks the clutch in the absence of foot pressure. An actuator means is employed for positively engaging and moving the operator member into its positions in response to pressure being placed on the foot. In a preferred embodiment, the operator member includes an operator ring carried concentric with the outer bearing race having a plurality of radial grooves formed in the inner periphery thereof which receive the roller bearings and positively position them in the above described first and second positions within the camming portions of the bearing race.

Drag means connected between the shaft and lower leg section imposes a drag force against rotation of the lower leg portion to control the swing speed thereof. In a preferred form, the drag means includes an expandable drag bushing carried within a hollow interior of the shaft which is connected to the lower leg portion by means of a stabilizer bar. Adjustable wedge means is provided for expanding the bushing against the shaft interior to vary the friction between the drag bushing and the interior of the shaft thereby adjusting the drag force on the lower leg section and, hence, the swing speed thereof.

DESCRIPTION OF THE DRAWINGS

The construction designed to carry out the invention will be hereinafter described, together with other features thereof.

The invention will be more readily understood from a reading of the following specification and by reference to the accompanying drawing(s) forming a part thereof, wherein an example of the invention is shown and wherein:

FIG. 1 is a perspective view illustrating kneejoint structure according to the invention for joining the upper and lower leg sections of a leg prosthesis shown in phantom lines;

FIG. 2 is a sectional view taken along line 2—2 of FIG. 1;

FIG. 5 is an elevation view with parts in section illustrating a roller clutch bearing assembly and operator member according to the invention which is illustrated in an unlocked position in which the clutch is inoperative permitting rotation about the center shaft in any direction;

FIG. 6 is an elevation view with parts in section illustrating the roller clutch bearing assembly of FIG. 5 in which the operator member is in a clutch position in which the operator member and clutch are in an operative locking position in response to pressure on the foot section of the prosthesis in a direction shown by the arrow.

FIG. 7 is an enlarged elevation illustrating the positioning of roller bearings in camming portions of a bearing race which controls the rotational action of a knee joint according to the invention;

FIG. 8 is an elevation view illustrating an operator ring member constructed according to the invention; and FIG. 9 is a sectional view of an alternate embodiment of a return aid connected between the knee joint and the lower leg section to control the swing of the lower leg section.

DESCRIPTION OF A PREFERRED EMBODIMENT

Figure 3:
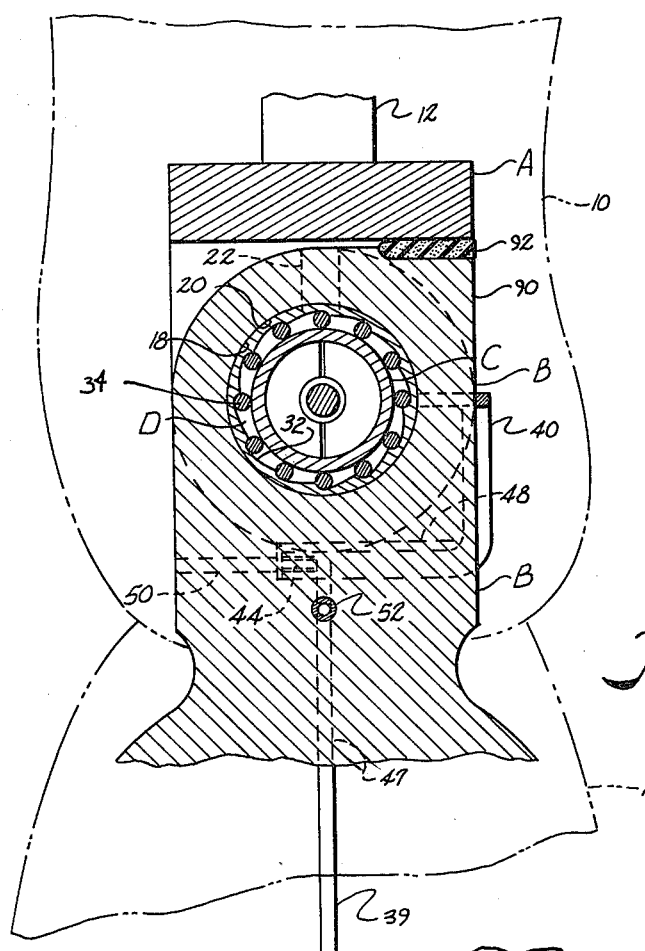
FIG. 3 is a sectional view taken along line 3—3 of FIG. 2.
Figure 4:
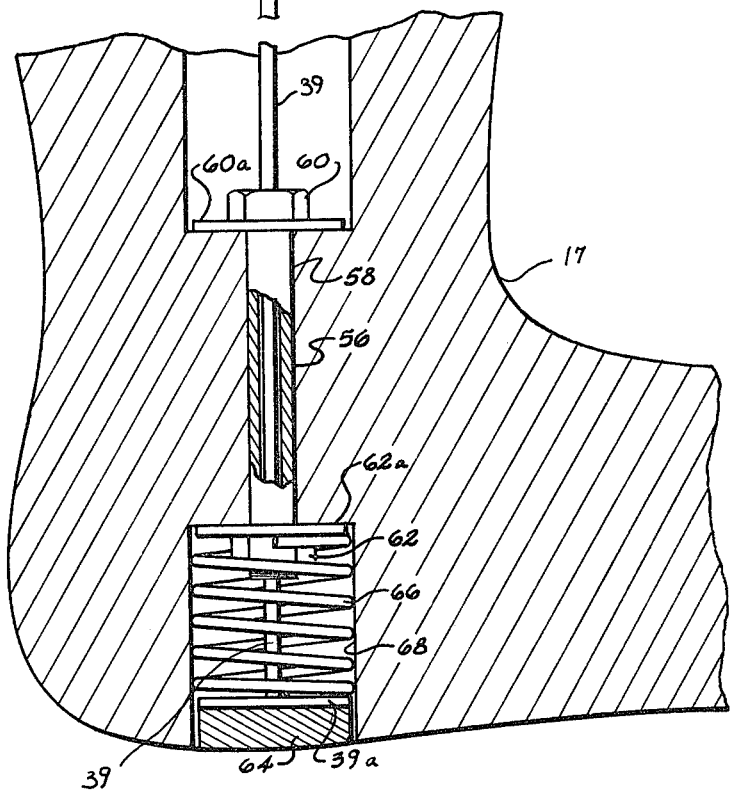
FIG. 4 is a partial sectional view of a foot section of a leg prosthesis incorporating means for actuating and controlling rotation of an artificial knee joint according to the invention as shown and aligned with FIG. 3.

The invention relates to rotary joints for artificial limbs which is particularly suitable for knee-joint structure in a leg prosthesis wherein control and locking of the knee joint is accomplished in response to pressure on the heel of a foot prosthesis. The simplicity and reliability of the artificial knee-joint structure, according to the present invention, makes possible a very inexpensive, lightweight, and durable leg prosthesis. Due to the miniature size and excellent control of the rotary joint apparatus according to the present invention, it is possible that such may be used in a wrist and hand prosthesis.

Referring to the drawing, a yoke member A is disclosed as connected to the upper leg section of the leg prosthesis and a housing member B is connected to the lower leg section of the prosthesis. A shaft C connects the yoke and housing members. A roller bearing clutch assembly, designated generally as D, is carried within the housing member B and receives the shaft C. The roller clutch assembly includes an outer bearing race pressed into the housing member B which includes a plurality of circumferentially spaced tapered camming portions having a generally wedge-shaped camming surface. A plurality of roller bearings are positioned in the camming portions between the camming surface thereof and the shaft. The roller bearings have a first position in the camming portion in which the bearings are urged by the camming surface against the shaft locking same together, preventing rotation about the shaft in a first direction. The roller bearings have a second position in the camming portion in which the bearings occupy the space of maximum depth of the tapering cam surface in which the rollers are freed allowing rotation about the shaft in any direction.

An operator member E is carried concentric with the outer bearing race about the shaft which includes a plurality of radial grooves in which the roller bearings are disposed and by which the roller bearings are positioned in the camming portions of the outer bearing race. The clutch operator member has a first clutching position in which the rollers are held in their first position and a second position in which the roller bearings are maintained in their second position rendering the clutch inoperative and allowing the lower leg section to rotate in any direction about the shaft. An actuator member F, responsive to pressure on a portion of a foot prosthesis, actuates and positions the operator member in its first and second positions. Pressure applied to the foot section actuates member F and positions the clutch operator to allow the clutch assembly to perform a normal clutching function, locking the bearing and shaft together, preventing rotation of the lower leg section in a first direction about the shaft which corresponds to the folding direction of the lower leg section.

Referring now in more detail to the drawing, FIG. 1, illustrates a yoke member A being secured to upper leg section 10 of the leg prosthesis by means of tubular fastener member 12 secured in any suitable manner and housing member B is secured by means of integral plate 14 to the lower section of the prosthesis 16 by any suitable fastening means. Housing B and plate 14 are preferably as one piece construction. Annular outer bearing race 18 is pressed within a hollow bore 20 formed in housing B and may be secured therein by means of a pin 22 extending through the outer wall of housing member B. Bearings 24 and 26 carried on opposing sides of the outer race 18 allow a smooth rotation between the housing B and the shaft C and also bear the load between the housing and the shaft and maintain a desired clearance between the rotation of the shaft and housing. Bearings 24 and 26 may be any conventional ring bearings. Shaft C is the pivot of the knee joint and pins 28 prevent rotation of the shaft within the yoke housing member A. The pins are pressed into flats 30 formed in the outer diameter of the shaft C. Alternately, pin holes 28 may be threaded for receiving set screws which fit in counter bores formed in shaft C.

Outer race 18 includes a plurality of circumferentially spaced camming portions 32 (FIG. 3) in which roller bearings 34 are positioned and carried between the camming surface of the camming portions 32 and the shaft C. Each camming portion 32 includes a tapering, generally wedge-shaped, camming surface having a portion of maximum depth generally at 32a and a taper narrowing portion at 32b. Under clutch operation, upon a slight movement of the lower leg section 16 about shaft C in a first direction, which corresponds to the folding direction of the lower leg section (clockwise), the outer race 18 secured to section 16 will likewise rotate clockwise whereby the roller bearings 34 will be wedged into the tapered area 32b between the camming surface and the shaft preventing clockwise rotation and folding of the lower leg section 16. However, rotation of the lower leg section 16 counterclockwise and thus rotation of the housing and outer race 18 counterclockwise is permitted since, in this movement, the roller bearings 34 will occupy the area of maximum depth 32a in the camming portions allowing them to rotate freely on the shaft. Camming portions 32 are cut out along the entire length of the bearing race 18.

As illustrated, clutch operator member E includes a pair of concentric operator rings 36 carried on opposing ends of the outer race 18 and rotate therewith. Each operator ring 36 includes a plurality of radial grooves 38. The roller bearings 34 are longer than the outer race 18, and the extended ends of the roller bearings 34 are received in the radial grooves 38 of the operator rings 36. Thus, by rotation of the operator ring 36, the position of the roller bearings within the camming portions of the fixed outer race 18 may be determined. In the second unlocking position of the operator rings 36, the operator rings hold roller bearings 34 in the portion 32a of the camming portions 32 and rotation of the housing B and lower leg section 16 in relation to the shaft C is permitted in any direction. With the operator ring 36 in the second position, the roller bearings and clutch assembly would appear and be held in the positions shown in FIG. 5 and full line position of FIG. 7. FIG. 6 corresponds to the first position of the operator rings 36 in which the rollers are positioned in camming portions 32b and operate in a one-way clutching mode to wedge against shaft C and prevent rotation in the folding rotation of leg section 16. Rollers 34 fit tightly in grooves 38 giving precision and positive control over roller positioning and clutch operation. The depth of the radial slots 38 provides a bearing effect for easy rotation of the operator ring 36 by actuator F.

Actuator means F is disclosed as including an operator rod 39 connected to an actuator member 40. The actuator rod is received in an opening 42 formed in arm 40a of the actuator member 40 and fixed therein by means of a set screw 44. Carried at the end of arm 40b of the actuator member is a fork 46 having a pair of arms 46a and 46b which are each received in an indent 36a formed in operator rings 36 on opposing sides of the outer race 18. The operator rings are kept in position by retainer rings 37.

The actuator rod 39 extends centrally in a bore 47 through the plate 14. The actuator member 40 is likewise carried in the housing in a bore 48 formed in the housing B and a bore 50 formed in the housing B provides for insertion and access to the set screw 44. A guide bushing 52 is inserted transverse to the actuator rod 39 and includes an opening through which the actuator rod 39 extends. The guide bushing 52 may be any bushing material such as plastic which serves as a bushing and guide for the reciprocation of the rod 39. It will be noted that the bore 48 is somewhat larger than the diameter of the arm 40a so that a lifting action may be imparted to the actuator member 40 and arms 46 which rocks the operator member into and out of its first and second positions.

The actuator rod 39 extends down to the foot section 17 of the prosthesis, which is integral or one-piece with section 16, through a guide bushing 56 secured in a bore 58 by means of nuts 60 and 62 threaded onto opposing ends of the bushing 56 and nut 60 serves to attach the foot section to the lower leg section. Washers 60a and 62a are positioned beneath the respective nuts. The actuator rod 39 terminates in an integral head portion 39a which serves as a base for a cushion material 64 occupying a heel portion of the foot prothesis. The cushioning material may be any suitable rubber or like resilient material. A spring 66 is carried between the washer 62a and the head 39a of the actuator rod and is contained by the sides of bore 68 formed in the foot section. The spring biases the actuator rod 39 downwardly and, hence, the actuator member 40 to position clutch operator rings 36 in their second position which corresponds to the unlocked position shown in FIG. 5 in which outer race 18 and housing B are free to rotate in any direction. Free rotation is constrained only by the drag system. When pressure is applied to the cushion 64 by means of the leg prosthesis being fully extended and the wearer's weight being placed thereon, the actuator rod 39 is moved up causing the actuator member 40 to rock the operator rings 36 to their first position allowing the roller clutch to perform its clutch function which is to lock and prevent rotation of the lower leg section 16 in the folding direction. Thus, direct positioning of clutch operator means E is effected by actuator F to positively position rollers 34 in either their first or second positions in the camming portions 32.

Means for imposing a drag to control the swing of the lower leg section 16 is provided by a pair of stabilizer bars 70 connecting the shaft and the lower leg section 16. The drag means further includes an expandable drag bushing 72 carried within a hollow interior portion 74 of the shaft C adjacent opposing ends thereof. The drag bushing is made of an expandable friction material such as plastic or the like and includes a tapered portion 74a in which a tapered wedge means 76 is received. A rod 78 having threaded ends extends through the hollow interior of the shaft, the wedge 76 and the threaded ends are secured by means of threaded caps 80 which connect the stabilizer bar 70. Stabilizer bars 70 include a mounting slot having a flat upper edge 70a which mates with a corresponding flat on bushing 74 for interlocking attachment therebetween. The remote ends of bars 70 are connected to the wood of lower leg section 16 by any suitable means such as screws (not shown). Drag tension is adjusted by shims 81 and held between the wedge bushing 76 and threaded cap 80. By turning the threaded caps 80, the position of the wedge members 76 in the drag bushings 72 may be adjusted so as to adjust the radial expansion of the drag bushings. As the drag bushings are expanded, more friction is created between the drag bushings and the shaft C, the connection between the drag bushings and the lower leg section 16 affords an adjustable drag force on the lower leg section as it swings to control the swing speed and thus produce a natural gait. If desired, the drag bushing may be expanded to provide a tight fitting in which a rigid pivoting of the knee joint is produced.

In an alternate embodiment illustrated in FIG. 9, spring 82 carried within the hollow interior 74 of the shaft C is utilized as a return aid to control the swing of lower section 16. One end of the spring is secured to cap member 80, and the other end of spring is secured to the shaft C at 84. The spring tension biases the lower leg section to a straight position and allows some flexibility in the leg swing. Stabilizer bars 70 are connected by the threaded caps 80 and a bushing 86 carried by a threaded caps in a like manner as described above.

Housing B includes an upper cam lobe 90 which, together with the underneath portion of yoke member A, provides a stop which limits rotation of lower section 16 in the counterclockwise direction. A resilient material 92 cushions the stop action and reduces noise. Pad 92 also aids in unlocking rollers 34 from their clutching or antirotational position.

OPERATION

In operation, at the beginning of a forward step of the leg prosthesis, the person will begin lifting the leg from the ground and swinging the upper section 14 of the prosthesis. This initiates bending of the knee joint. As leg section 14 swings, drag bushing friction is overcome allowing rotation of the lower leg section 14 in the direction of folding (clockwise) relative to the knee joint. Since there is no weight on the foot section of the prosthesis, the actuator rod 39 is under the action of the spring 66 and the operator rings 36 are in the second position in which they unlock the roller clutch assembly D permitting free rotation of the knee joint in any direction. As the leg prosthesis straightens out, the rotation of the knee joint is terminated as stop 90 is reached. The leg is maintained in the straight position by the stabilizer bars 70 and drag system until heel cushion 64 contacts the ground. The weight of the person is then on the leg prosthesis depressing the cushion material 64, thus lifting the actuator rod 39 upwards. This lifts the actuator arm 40 rocking the operator rings 36 into their first position, placing the roller clutch assembly D in its clutching mode of operation in which the lower leg section 14 is locked against moving in the folding direction. Further pressure on the foot is absorbed by compression of the cushion whereby sensitive operation of the actuator may be had. Should lower leg section 16, as attached to the housing B, tend to rotate in the folding or clockwise direction, outer race 18 would rotate clockwise camming the rollers 34 between the tapered area 32b of the camming surface and the shaft C locking any rotation between the housing B and the shaft C. Shifting of the body weight from the heel to toe of the foot produces a counterclockwise force at the knee joint which compresses pad 92 slightly and allows the wedging force on rollers 34 to be somewhat relieved, allowing spring 66 to more reliably return the actuator rod 39 downwardly. Downward movement of rod 39 moves operator rings 36, through actuator member 40, to their override position in which the lower leg section is again free to rotate in any direction.

It will be seen that the above described knee joint and control thereof provide the advantage that any time the wearer of the leg prosthesis removes weight from the foot, the knee joint will be completely free to operate so that the lower leg section may be folded as required for sitting and other non-supportive maneuvers.

While a preferred embodiment of the invention has been described using specific terms, such description is for illustrative purposes only, and it is to be understood that changes and variations may be made without departing from the spirit or scope of the following claims.

What is claimed is:

1. Knee-joint apparatus for a leg prosthesis having an upper leg section above and a lower leg section below the knee joint, said apparatus comprising:
   a connecting member connected to one of said upper or lower leg sections;
   a housing member connected to the other of said upper and lower leg sections;
   a shaft rotatably connecting said connecting and housing members;
   a roller bearing clutch assembly rotatably connecting said housing member to said shaft including:
   an outer bearing race connected to said housing member including a plurality of circumferentially spaced tapered camming portions having a generally wedge-shaped camming surface;
   a plurality of roller bearings position in said camming portions bearing against said shaft;
   said roller bearings having a first position in said camming portion in which said bearings are locked between a surface of the camming portion and said shaft for locking and preventing rotation relative to said shaft in a first direction;
   said roller bearings having a second position in said camming portion in which said bearings are freed between said camming portion surface and said shaft permitting rotation between said shaft and housing member;
   a clutch operator means carried concentric with said shaft operatively connected with said roller bearings for shifting said position of said roller bearings in said camming portions, said operator means having an unlocked position in which said clutch assembly in disengaged and said roller bearings are held in said second position to permit rotation in said first direction;
   said clutch operator means having a locked position in which roller bearings are maintained in said first position thereof and prevent said rotation in said first direction;
   said clutch operator means including a first operator ring carried on one end of said bearing race and a second operator ring carried on an opposing end of said bearing race, said first and second operator rings being carried about said shaft concentric with said bearing race, and said roller bearings having opposing ends fixed in said operator rings and wherein said operation rings including a mechanical connection to actively engage an actuator member in response to pressure on a portion of said foot prosthesis for positioning said bearings in said first and second positions; and
   said actuator member including a rigid mechanical linkage assembly connected between said foot prosthesis having a pair of prongs, one each of said prongs engaging said first and second operator rings to positively position said rings and roller bearings held thereby.

2. A controlled roller clutch apparatus for use in rotary joints of the type used in a prosthesis and the like having first and second sections which are interconnected by a shaft and rotate relative to one another, said apparatus comprising:
   an outer bearing race for being affixed to said first section, said bearing race having an interior surface;
   a plurality of camming portions formed in said interior of said outer bearing race;
   a plurality of roller bearings positioned within said camming portions and between said outer race and said shaft;
   said roller bearings having a first position in said camming portion wherein said camming portion urges said roller bearings against said shaft and prevents relative rotation between said shaft and said first section in a first direction;
   said roller bearings having a second position in said camming portion wherein said rollers are freely rotatable and relative rotation between said shaft and said bearing race is permitted in any direction;
   a clutch operator means carried concentric with said shaft operatively connected with said roller bearings for shifting said position of said roller bearings in said camming portions, said operator means having an unlocked position in which said clutch assembly is disengaged and said roller bearings are held in said second position to permit said relative rotation in said first direction;

said clutch operator means having a clutch mode position in which said roller bearings are allowed to occupy said first position thereof and prevent said relative rotation in said first direction;

an actuator member for positively engaging said operator means and positioning said operator means in said unlocked and clutch mode positions;

said clutch operator means including a first operator ring carried on one end of said bearing race and a second operator ring carried on an opposing end of said bearing race, said first and second operator rings being carried about said shaft concentric with said bearing race, and said roller bearings having opposing ends fixed in said operator rings and wherein said operator rings further include a mechanical connection to actively engage said actuator member in response to pressure on a portion of said foot prosthesis for positioning said bearings in said unlocked and clutch mode positions; and said actuator member including a rigid mechanical linkage assembly having a pair of prongs engaging said first and second operator rings to positively position said rings and roller bearings held thereby.

* * * * *